(12) United States Patent
Zhang et al.

(10) Patent No.: US 8,170,654 B1
(45) Date of Patent: May 1, 2012

(54) SEQUENTIAL DISCRIMINATION APPROACH FOR DETECTING TREATABLE CARDIAC RHYTHMS

(75) Inventors: Xusheng Zhang, Shoreview, MN (US); Robert W. Stadler, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 43 days.

(21) Appl. No.: 12/903,325

(22) Filed: Oct. 13, 2010

(51) Int. Cl.
*A61B 5/046* (2006.01)
*A61B 5/0464* (2006.01)

(52) U.S. Cl. ......... 600/518; 600/508; 600/509; 600/515
(58) Field of Classification Search .................. 600/508, 600/509, 515, 518
See application file for complete search history.

(56) References Cited

U.S. PATENT DOCUMENTS

| | | | |
|---|---|---|---|
| 5,411,530 A | 5/1995 | Akhtar | |
| 5,991,656 A | 11/1999 | Olson | |
| 6,212,428 B1 | 4/2001 | Hsu | |
| 6,275,732 B1 | 8/2001 | Hsu | |
| 6,393,316 B1 | 5/2002 | Gillberg | |
| 6,430,435 B1 | 8/2002 | Hsu | |
| 7,050,846 B2 * | 5/2006 | Sweeney et al. | 600/515 |
| 7,206,633 B2 * | 4/2007 | Saba | 607/14 |
| 7,537,569 B2 | 5/2009 | Sarkar | |
| 7,769,436 B1 | 8/2010 | Boileau et al. | |
| 2002/0120306 A1 | 8/2002 | Zhu et al. | |
| 2007/0232945 A1 | 10/2007 | Kleckner | |
| 2007/0239044 A1 * | 10/2007 | Ghanem et al. | 600/509 |
| 2008/0269624 A1 | 10/2008 | Zhang | |

FOREIGN PATENT DOCUMENTS

| | | |
|---|---|---|
| EP | 2371280 A1 | 5/2011 |
| WO | 01/24876 A1 | 4/2001 |

OTHER PUBLICATIONS (PCT/US2011/055732) PCT Notification of Transmittal of the International Search Report and the Written Opinion of the International Searching Authority.

\* cited by examiner

*Primary Examiner* — Carl H Layno
*Assistant Examiner* — Yun Haeng Lee
(74) *Attorney, Agent, or Firm* — Michael C. Soldner

(57) ABSTRACT

A system and method for use in a medical device for discriminating cardiac events establishes population-based thresholds corresponding to cardiac signal morphology metrics for discriminating between a first cardiac event and a second cardiac event. A population-based threshold criterion for discriminating cardiac events is established. The population-based threshold criterion is applied to a cardiac signal segment and the segment is classified if the criterion is satisfied. A patient-specific threshold is established in response to the sensed cardiac signal segment not being classified after applying the population-based threshold criterion. The sensed signal segment is classified in response to the patient-specific threshold comparison.

25 Claims, 10 Drawing Sheets

SEQUENTIAL DISCRIMINATION APPROACH FOR DETECTING TREATABLE CARDIAC RHYTHMS

TECHNICAL FIELD

The disclosure relates generally to implantable medical devices and, in particular, to a method and apparatus for discriminating treatable and non-treatable cardiac rhythms.

BACKGROUND

A typical implantable cardioverter defibrillator (ICD) has the capability of providing a variety of anti-tachycardia pacing (ATP) regimens as well as cardioversion/defibrillation shock therapy. Normally, arrhythmia therapies are applied according to a pre-programmed sequence of less aggressive to more aggressive therapies depending on the type of arrhythmia detected. Typically, termination of an arrhythmia is confirmed by a return to either a demand-paced rhythm or a sinus rhythm in which successive spontaneous R-waves are separated by at least a defined interval. When ATP attempts fail to terminate the tachycardia, high-voltage cardioversion shocks may be delivered. Since shocks can be painful to the patient and consume relatively greater battery energy than pacing pulses, it is desirable to avoid the need to deliver shocks by successfully terminating the tachycardia using less aggressive pacing therapies. On the other hand, if a tachycardia is a lethal arrhythmia that is likely to require a shock therapy for successful termination, it is desirable to deliver the shock therapy as quickly as possible without delay.

The success of a tachycardia therapy depends in part on the accuracy of the tachycardia detection. In some cases, a tachycardia originating in the atria, i.e. a supraventricular tachycardia (SVT), is difficult to distinguish from a tachycardia originating in the ventricles, i.e. a ventricular tachycardia (VT). For example, both the atrial chambers and the ventricular chambers may exhibit a similar tachycardia cycle length when an SVT is conducted to the ventricles or when a VT is conducted retrograde to the atria.

Accordingly, accurate classification of a detected tachycardia as VT or SVT is needed in order to properly determine when and what type of therapy is necessary. As more complex algorithms become available for accurately detecting and discriminating cardiac rhythms with a high sensitivity and high specificity, the processing time and burden on the ICD for performing these algorithms increases. These relatively more complex algorithms may be needed when the rhythm type is difficult to discern. At times, however, more complex algorithms may pose undue processing burden. What is needed, therefore, is a method and apparatus for discriminating SVT and VT with high sensitivity and specificity while limiting the signal processing burden.

DETAILED DESCRIPTION

Figure 1:
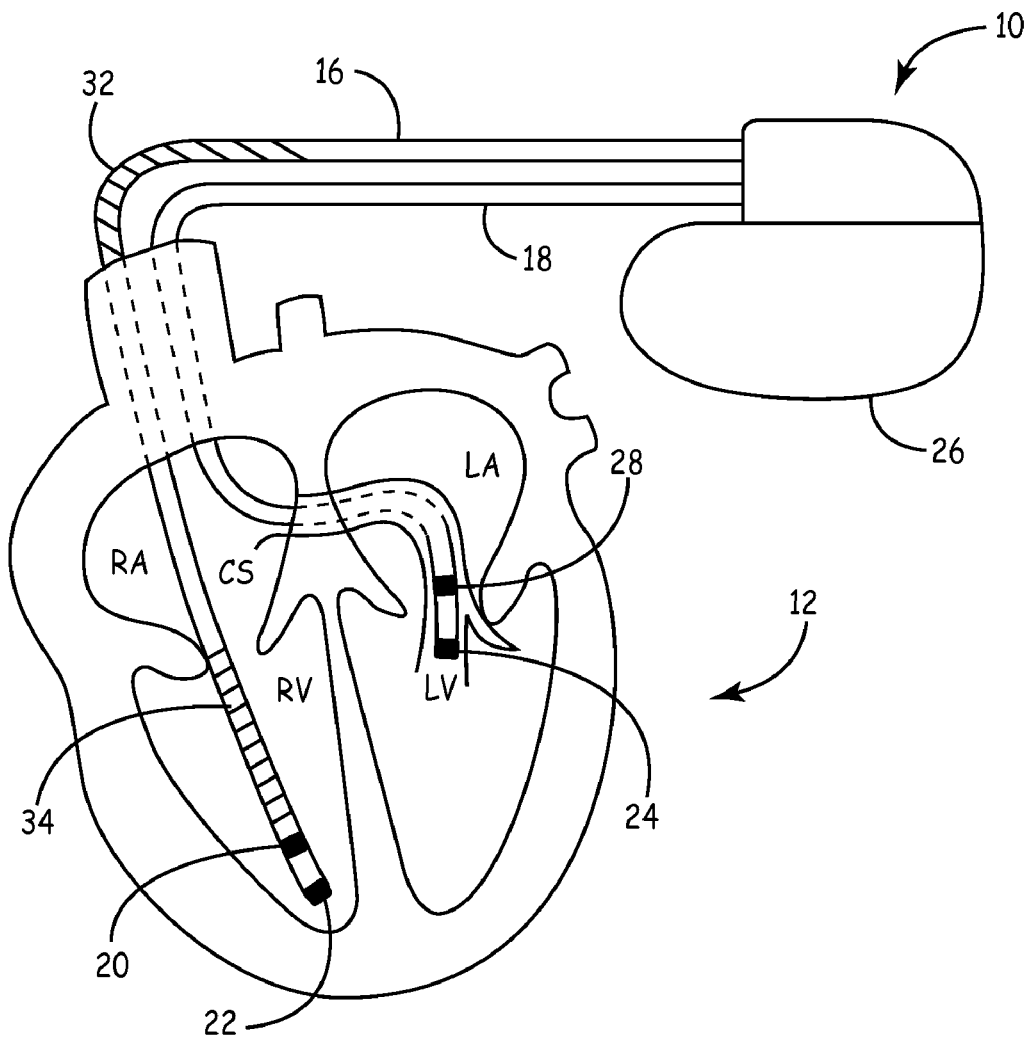
FIG. 1 is a schematic representation of an implantable medical device (IMD).

In the following description, references are made to illustrative embodiments. It is understood that other embodiments may be utilized without departing from the scope of the disclosure. In some instances, for purposes of clarity, identical reference numbers may be used in the drawings to identify similar elements.

FIG. 1 is a schematic representation of an implantable medical device (IMD) 10. IMD 10 is embodied as an ICD in FIG. 1. Methods described herein, however, should not be interpreted as being limited to any particular implantable medical device or any particular cardiac medical device. Instead, embodiments may include any cardiac medical device so long as the device utilizes a plurality of electrodes or other sensors for monitoring the cardiac rhythm of a patient.

In FIG. 1, the right atrium (RA), left atrium (LA), right ventricle (RV), left ventricle (LV), and the coronary sinus (CS), extending from the opening in the right atrium to form the great cardiac vein, are shown schematically in heart 12. Two transvenous leads 16 and 18 connect IMD 10 with the RV and the LV, respectively. Each lead includes at least one electrical conductor and pace/sense electrode. The electrodes are capable of sensing cardiac EGM signals, also referred to herein generally as "cardiac signals", and delivering electrical pacing pulses to the cardiac tissue. For example, leads 16 and 18 are connected to pace/sense electrodes 20, 22, and 24, 28, respectively. In addition, a housing electrode 26 can be formed as part of the outer surface of the housing of the device 10. The pace/sense electrodes 20, 22, and 24, 28 and housing electrode 26 can be selectively employed to provide a number of unipolar and bipolar pace/sense electrode combinations for pacing and sensing functions. The depicted positions in or about the right and left heart chambers are merely illustrative. Moreover, other leads and pace/sense electrodes can be used instead of, or in combination with, any one or more of the depicted leads and electrodes.

Typically, in pacing systems of the type illustrated in FIG. 1, the electrodes designated herein as "pace/sense" electrodes are used for both pacing and sensing functions. In certain embodiments, these electrodes can be used exclusively as pace or sense electrodes in programmed or default combinations for sensing cardiac signals and delivering pace pulses. The leads and electrodes described can be employed to record cardiac signals. The recorded data can be periodically transmitted to a programmer or other external device enabled for telemetric communication with the IMD 10.

An RV coil electrode 34 and a superior vena cava (SVC) coil electrode 32 are also shown as being coupled to a portion of RV lead 16. Coil electrodes can additionally or alternatively be coupled to portions of CS lead 18. The coil electrodes 32 and 34, or other similar electrode types, can be electrically coupled to high voltage circuitry for delivering high voltage cardioversion/defibrillation shock pulses.

Electrodes shown in FIG. 1 can be disposed in a variety of locations in, around, and on the heart and are not limited to the locations shown. ICDs and pacemakers typically use a ventricular EGM signal for sensing ventricular events (R-waves) for determining a need for pacing and for detecting a RR intervals meeting tachycardia detection criteria. An EGM sensing vector may be a unipolar or bipolar sensing vector using one or two electrodes, respectively, placed in or on the heart chambers.

Embodiments described herein are not limited to use with intracardiac or transvenous leads as shown in FIG. 1. Subcutaneously implanted electrodes or even external electrode systems may be used. As used herein, the term "cardiac signal" refers generally to any cardiac electrical signal sensed using any electrodes, including an EGM signal or an ECG signal. Reference is made to U.S. Patent Publication No. 2007/0232945 (Kleckner) for a description of a subcutaneous ICD in which cardiac event discrimination methods described herein may be implemented. The '945 publication is incorporated herein by reference in its entirety Furthermore, other transvenous lead and electrode systems may be substituted for the system shown in FIG. 1. A detection algorithm may or may not use electrodes for sensing atrial signals for detecting and discriminating treatable rhythms. IMD 10 is shown coupled only to ventricular leads 16 and 18 but implementation of a selected detection algorithm is not limited to systems employing only ventricular leads. Additional electrodes may be positioned for sensing atrial event (P-waves) and determining PP intervals, PR intervals and/or RP intervals. In other embodiments, dual chamber or multi-chamber systems may be used which include atrial leads used to position electrodes in, on or around the atrial chambers. Systems that employ atrial leads without the use of ventricular leads may also be used depending on the algorithm implemented for detecting arrhythmia episodes and according to patient need.

Figure 2:
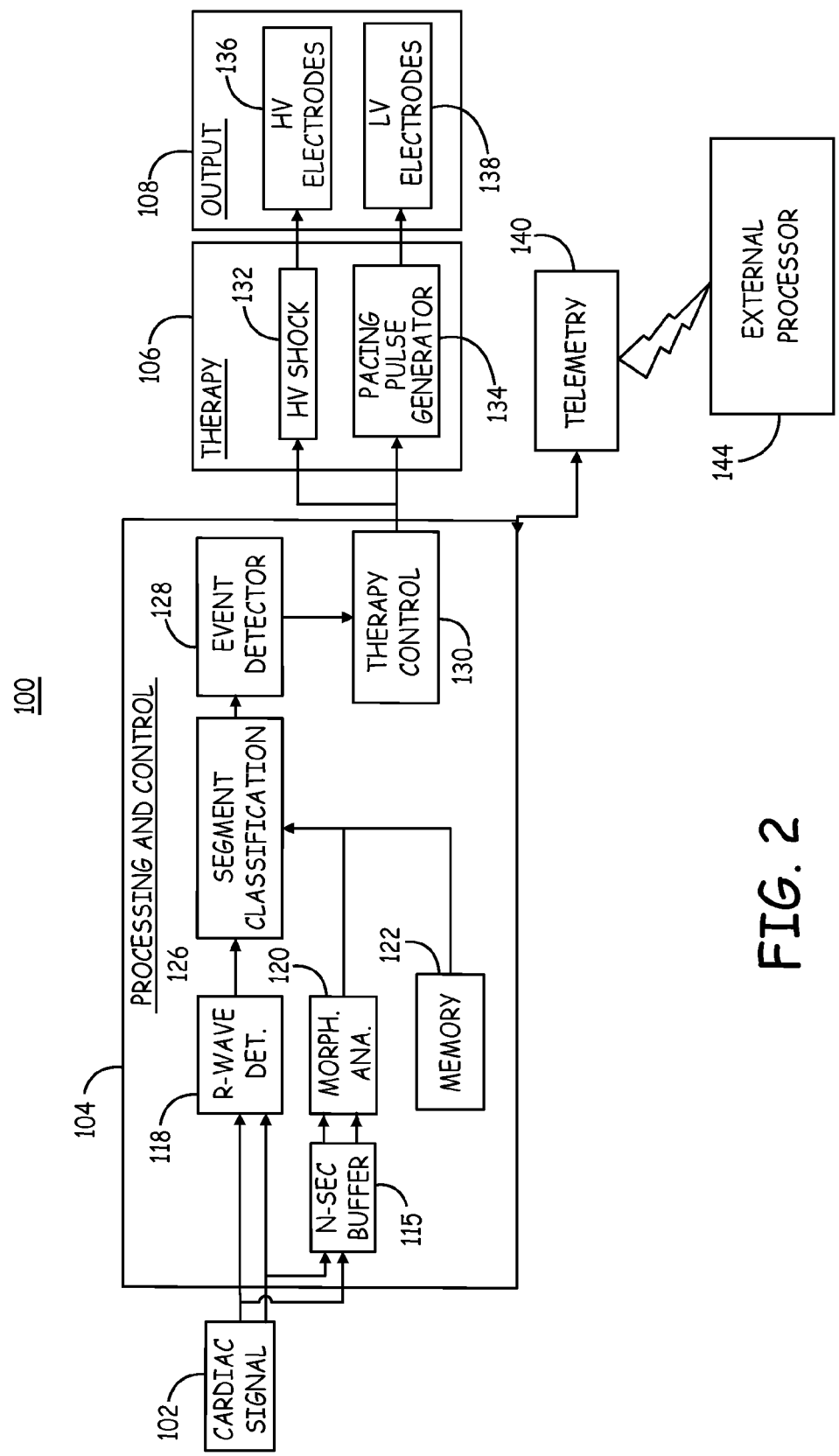
FIG. 2 is a functional block diagram of electronic circuitry that is included in one embodiment of an IMD for practicing the methods described herein.

FIG. 2 is a functional block diagram 100 of electronic circuitry that is included in one embodiment of an IMD for practicing the methods described herein. IMD 100 includes cardiac signal input 102, processing and control 104, therapy module 106, output 108 and telemetry module 140. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Input 102 includes at least one cardiac signal sensed to provide input to processing and control 104 for detecting cardiac events. Input 102 may include one or more EGM and/or ECG sensing electrode vectors for obtaining cardiac signals. Other physiological sensors, such as pressure, flow, oxygen, or motion sensors, may be included in alternative embodiments for providing additional signals used to detect arrhythmias or monitoring other patient conditions. A sequential discrimination algorithm is described herein which relies exclusively on EGM and/or ECG signals, collectively referred to herein as "cardiac signals", however it is contemplated that other signals containing cardiac information may be substituted for an EGM or ECG signal or used in combination therewith.

Processing and control module 104, also referred to herein as a "controller", includes a buffer 115 which stores an n-second segment of a cardiac signal received from cardiac signal input 102. An R-wave detector 118 receives the cardiac signal input 102 for sensing R-waves and determining RR intervals. A morphology waveform analysis module 120 receives input from the n-second buffer to compute various morphology metrics from the buffered cardiac signal segment. As indicated above, practice of the methods described herein is not limited to a single ventricular cardiac signal but may be applied to multiple atrial and/or ventricular cardiac signals. For the sake of illustration, in the description that follows a single ventricular cardiac signal is used for cardiac event detection.

Segment classification module 126 classifies each cardiac signal segment as "treatable" or "non-treatable" based on R-wave intervals received from R-wave detector 118 and/or morphology analyzer 120. Segment classification module 126 utilizes a sequential discrimination method including a hierarchal sequence of classification criteria as will be described in detail below. In general, the sequence includes a set of comparisons beginning from less computationally intensive to more computationally intensive comparisons which allow discrimination of cardiac rhythms with the highest possible sensitivity and specificity and least processing power required. Additionally or alternatively, the sequence is ordered according to a highest probability or frequency of classifying a cardiac signal segment in response to applying the criterion for a given cardiac event type.

A "treatable" rhythm, as used herein, refers to any tachycardia that is ventricular in origin and can potentially be treated by delivering a therapy in the ventricles for terminating the ventricular tachycardia. A "non-treatable" rhythm is any rhythm with a relatively slow ventricular rate (below a ventricular tachycardia rate) and any tachycardia that is supraventricular in origin. Delivering a therapy only in the ventricular chambers frequently does not resolve a supraventricular tachycardia.

It is recognized, however, that depending on the particular application, the designations of "treatable" and "non-treatable" rhythms may be defined differently. For example, a device that is only programmed to deliver shock therapies may define treatable rhythms as those that require a cardioversion/defibrillation shock and non-treatable rhythms as those that are not treated with a shock. In cardiac devices capable of delivering atrial therapies, treatable rhythms may include some atrial arrhythmias.

In general, possible cardiac signal segment classifications may include SVT, normal sinus rhythm (NSR), sinus tachycardia, slow VT, fast VT, VF, or any subset or combination thereof, and these segment classifications can lead to a cardiac event detection, which may or may not result in therapy delivery depending on the therapy delivery capabilities of the particular device and programmed therapy regimens. In some embodiments, some of these classifications may be grouped into non-treatable and treatable classifications. For example, any classification of SVT or sinus tachycardia would be non-treatable and any classification of fast VT or VF would be treatable when the sequential discrimination algorithm is used to identify shockable cardiac events. A discrimination algorithm will provide discrimination between the treatable and non-treatable rhythms but may not provide further discrimination between the different treatable rhythm types and the non-treatable rhythm types, particularly when the decision to treat is a decision to shock or not shock.

An event detector 128 detects a treatable cardiac event when a required number of cardiac signal segments are classified as treatable. The therapy control module 130 responds to the detection of a cardiac event by controlling high voltage (HV) shock pulse generator 132 to deliver a cardioversion/defibrillation shock using high voltage electrodes 136 and/or by controlling pacing pulse generator 134 used to deliver pacing pulses using low voltage (LV) electrodes 138 as needed, e.g., for anti-tachycardia pacing, during a programmed menu of therapies including pacing and shock delivery, or during post-shock recovery. It is recognized that in some embodiments, any of the HV electrodes 136 and LV electrodes 138 in output 108 may also be used as sensing electrodes in input 102.

IMD 100 includes telemetry circuit 140 capable of bidirectional communication with an external device 144 such as a programmer or home monitor. Telemetry circuit 140 is used to transmit cardiac event data to an external programmer Cardiac signal data obtained by R-wave detector 118, morphology analyzer 120, and/or segment classification 126 may also be collected and transmitted to an external device for review and analysis. Uplink telemetry allows device status and diagnostic/event data to be sent to an external programmer or home monitor 144 for review by the patient's physician. Downlink telemetry allows the external device 144, via physician control, to enable programming of IMD function and the optimization of detection and therapy processes for a specific patient.

External device 144 may be embodied as an external processor used to collect cardiac signal data from a patient population and process the data to establish population-based threshold criterion for classifying cardiac signal segments. Methods for establishing population-based threshold criteria will be described in greater detail below.

Figure 3:
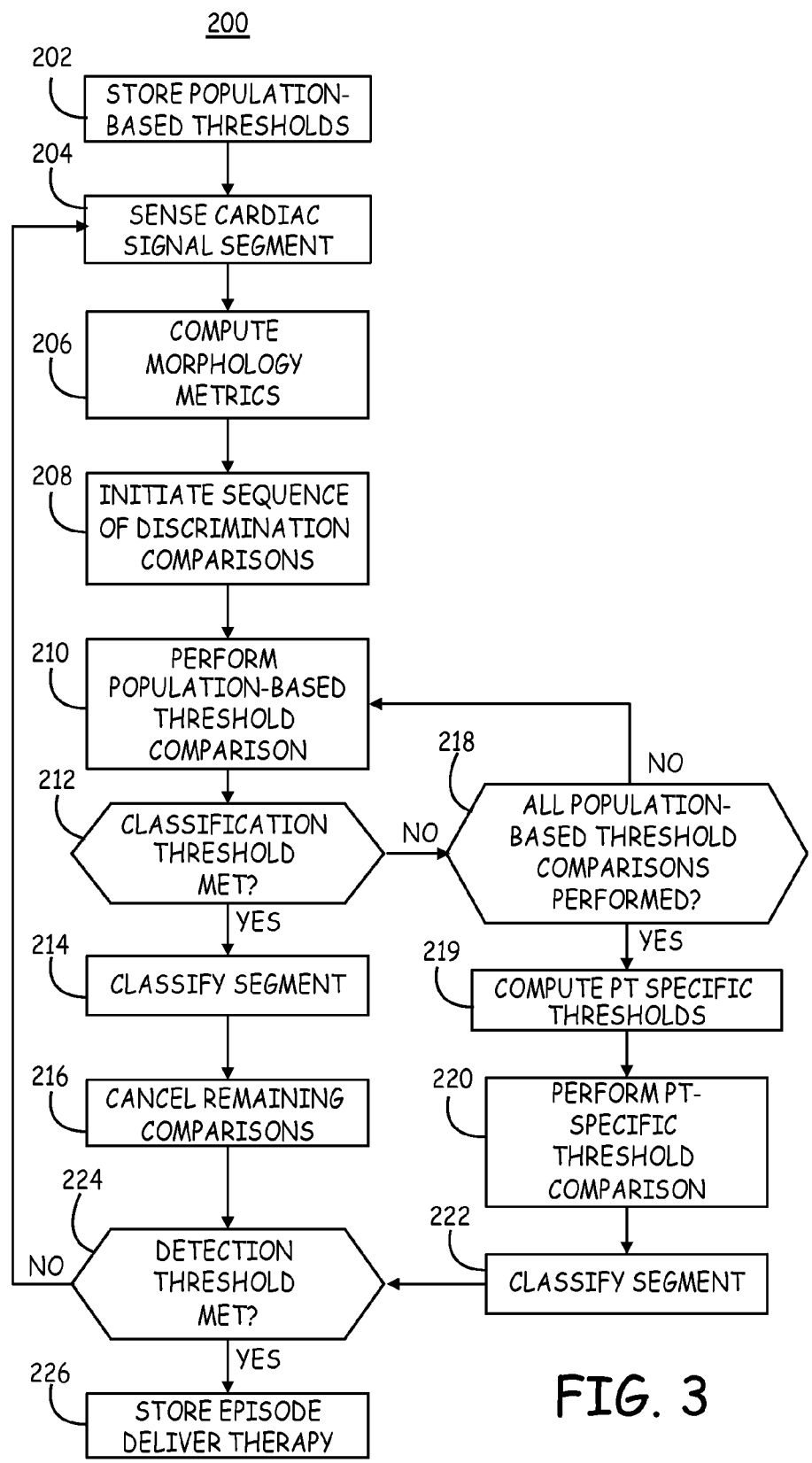
FIG. 3 is a flow chart of a method for classifying a cardiac signal for use in detecting cardiac events.

FIG. 3 is a flow chart 200 of a method for classifying a cardiac signal for use in detecting cardiac events. Flow chart 200 and other flow charts presented herein are intended to illustrate the functional operation of the device, and should not be construed as reflective of a specific form of software or hardware necessary to practice the methods described. It is believed that the particular form of software, firmware and/or hardware will be determined primarily by the particular system architecture employed in the device and by the particular detection and therapy delivery methodologies employed by the device. Providing software, firmware and/or hardware to accomplish the described functionality in the context of any modern medical device, given the disclosure herein, is within the abilities of one of skill in the art.

Methods described in conjunction with flow charts presented herein may be implemented in a computer-readable medium storing instructions for causing a programmable processor to carry out the methods described. A "computer-readable medium" includes but is not limited to any volatile or non-volatile media, such as a RAM, ROM, CD-ROM, NVRAM, EPROM, EEPROM, flash memory, and the like. The instructions may be implemented as one or more software modules, which may be executed by themselves or in combination with other software.

At block 202, population-based thresholds for cardiac signal characteristics are stored in the IMD for discriminating treatable and non-treatable rhythms. The thresholds are determined from clinical data acquired from a population of patients. Examples of determinations of population-based thresholds applied to cardiac signal characteristics will be described below in conjunction with FIGS. 4A-C, FIGS. 5A-B and FIG. 7.

At block 204, a cardiac signal is sensed and an n-second segment is buffered. In one embodiment, a 3-second signal is buffered from which morphology metrics are computed at block 206. The morphology metrics computed at block 206 are selected as the cardiac signal characteristics that provide the greatest confidence in separating treatable from non-treatable (or non-treatable from treatable) cardiac rhythms.

At block 208, a sequence of comparisons for classifying the cardiac signal segment is initiated using the computed morphology metrics and the stored population-based thresholds. While the blocks shown in FIG. 3 and in other flow charts presented herein are shown in a particular order, it is recognized that operations described may be performed in a different order than that shown and still reach a similar result. For example, the morphology metrics computed at block 206 may all be computed in advance of performing a sequence of comparisons at block 210 or may be computed as needed as the sequence of comparisons advances from one comparison to another.

If a threshold criterion is satisfied at decision block 212, the cardiac signal segment is classified accordingly at block 214. A classification threshold criterion requires a signal characteristic to either be greater than or less than the threshold with a resulting classification occurring only when the requirement is met. If the requirement is not met, no classification is made. The classification for a given threshold comparison may be related to either treatable or non-treatable segments but not both. For example, if the threshold requirement relates to classifying a treatable segment, a non-treatable segment classification will never be made in response to performing that particular threshold criterion. If the threshold criterion is satisfied, a classification of treatable is made. If the threshold requirement is not met, no classification is made at all. Other classification criterion may define a requirement for classifying a segment as a non-treatable segment. The result of applying the classification criterion will be either a non-treatable segment classification or no classification at all and will never result in a treatable classification. The population-based threshold comparisons may be described as "one-way" classification criteria because if a given criterion is not satisfied, no classification is made at all rather than giving a different classification. The cardiac signal segment is classified in response to applying a population-based threshold criterion only when the criterion is satisfied and otherwise remains unclassified. A population-based criterion may also be described as an IF/THEN operation. If the threshold criterion defines a threshold for classifying a treatable rhythm, the operation would be:

IF threshold met, THEN treatable.

If the threshold criterion defines a threshold for classifying a non-treatable rhythm, the operation would be:

IF threshold met, THEN non-treatable.

In either case, if the threshold is not met, no classification is made.

The sequence of comparisons initiated at block 208 begins with a first comparison that provides a relatively high confidence in rhythm separation, a relatively low computational burden, and a high frequency of classified segments after the first comparison. As used herein, a high degree of confidence may correspond to a confidence that approximately 80%, 90%, 95% or other acceptable percentage of all segments classified based on a population-based threshold comparison are classified correctly.

If the first classification criterion is satisfied and results in classifying the cardiac signal segment, the segment classification is made immediately at block 214 without applying additional classification criteria. When a classification threshold criterion is met, the remaining comparisons in the initiated sequence of population-based threshold criteria are cancelled at block 216.

After classifying the segment, cardiac event detection criteria are applied at block 224. Typically, in order to detect a treatable cardiac event, more than one cardiac signal segment out of a given number of the most recent segments must be classified as treatable. For example, if five out of eight of the most recent n-second segments are classified as treatable, a treatable episode is detected at block 224.

Data relating to the detected cardiac event is stored at block 226. Depending on the cardiac event being detected and the therapy delivery capabilities of the device, a therapy may be delivered in response to the detected event. If the cardiac event detection threshold is not met at block 224, the process returns to block 204 to evaluate the next cardiac signal segment.

If a classification threshold comparison does not result in a classification threshold being met at block 212, the process advances to block 218 to determine if all population-based threshold comparisons in the sequence have been performed. If not, the process returns to block 210 to perform the next comparison in the sequence.

If all of the population-based threshold comparisons have been performed in the sequence of comparisons (affirmative result at block 218), the process advances to block 219 to compute a patient-specific threshold using the current n-second cardiac signal segment and/or previously stored cardiac signal segments. Computation of a patient-specific threshold and performing a patient-specific threshold comparison in real-time may require greater processing burden than a comparison using a previously stored population-based threshold. As such, the less computationally-intensive population-based threshold comparisons are made first to determine if the segment can be classified with a relatively high degree of confidence based on empirically-derived thresholds. If a segment remains unclassified after completing the sequence of population-based threshold comparisons, the discrimination algorithm advances to a patient-specific threshold comparison.

After computing the patient-specific threshold at block 219, a patient-specific threshold comparison is performed at block 220. While not explicitly shown, it is to be understood that this comparison at block 220 may require one or more new cardiac signal characteristics or morphology metrics to be computed if not already computed at block 206 for the current cardiac signal segment.

Based on this patient-specific comparison, the current n-second segment is classified at block 222. The patient-specific threshold comparison will always result in a segment classification, and may be considered a "two-way" classification. If the patient-specific threshold criterion is not satisfied to classify the segment as a first cardiac event, the segment will still be classified as a second cardiac event. This is in contrast to the population-based threshold comparison that requires a threshold criterion to be met in order to make a classification; if the threshold criterion is not met, no classification is made at all. The patient-specific comparison may be thought of as an IF/THEN/ELSE operation wherein, if the threshold is defined to classify a treatable rhythm, the operation would be:

IF threshold met, THEN treatable, ELSE non-treatable.

The segment classification resulting from the patient-specific classification is used at block 224 to determine if the cardiac event detection threshold is met (e.g. required number of segments classified as treatable). If not the process returns to block 204. If a cardiac event is detected, the process advances to block 226 to store the cardiac event episode data and deliver an appropriate therapy as needed.

Figure 4A:
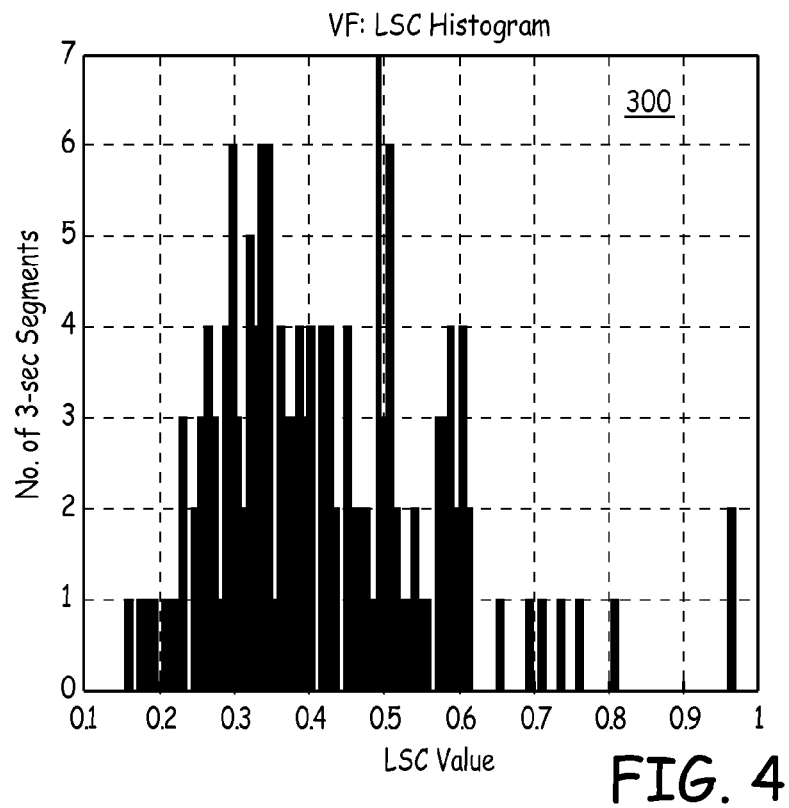
FIGS. 4A through 4C are histogram plots of the frequency of a morphology metric for ventricular fibrillation (VF) (FIG. 4A), VT (FIG. 4B) and SVT (FIG. 4C).
Figure 4B:
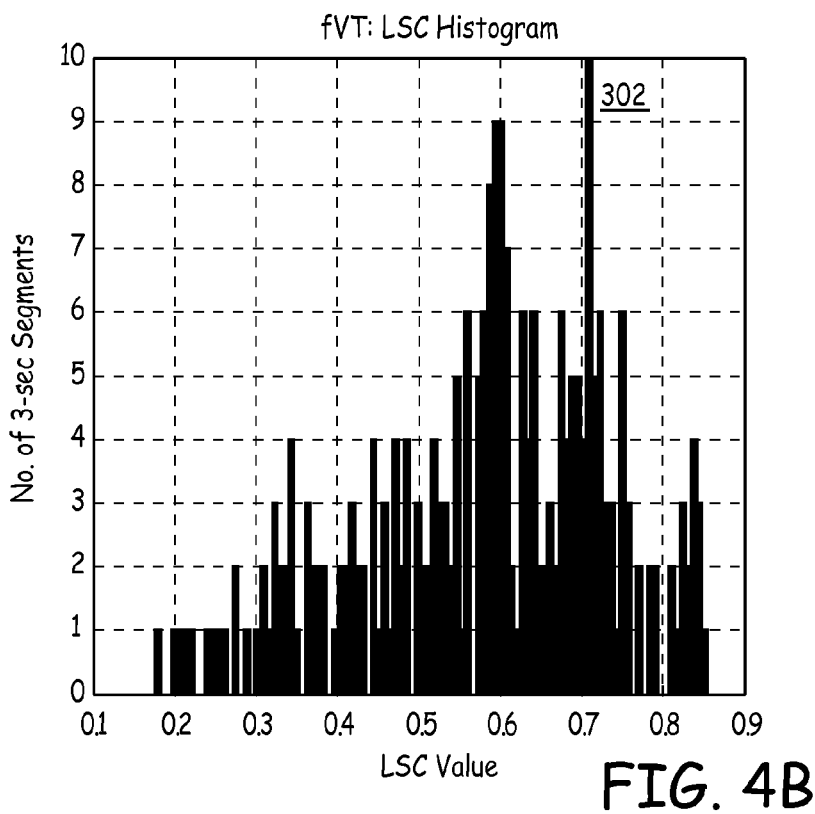
Figure 4C:
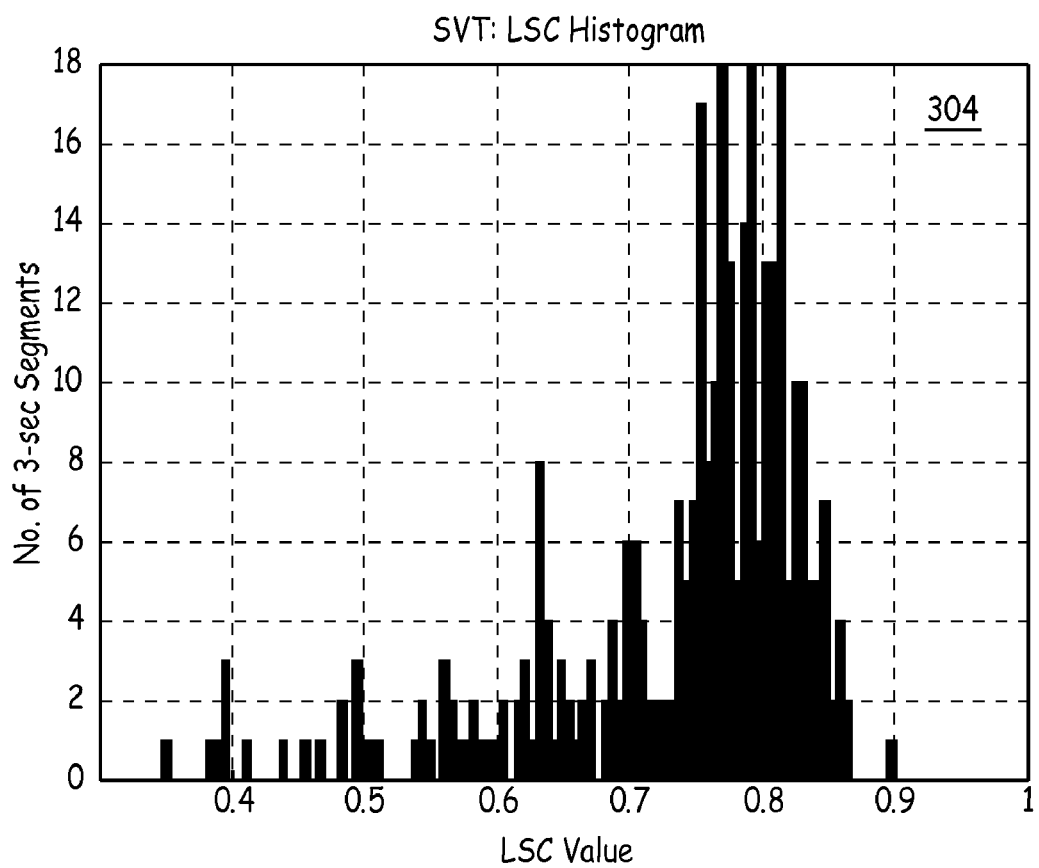

FIGS. 4A through 4C are histogram plots of a morphology metric for cardiac signal segments corresponding to VF (FIG. 4A), fast VT (FIG. 4B) and SVT (FIG. 4C). In this particular example, the morphology metric is a low slope content (LSC) computed from 3-second cardiac signal segments obtained from a population of patients. The LSC of a non-treatable tachycardia is typically high relative to the LSC of a shockable tachycardia. As such, the LSC is a useful morphology metric for discriminating between treatable and non-treatable rhythms.

The LSC may be computed according to methods generally described in U.S. Pat. Publication No. 2008/0269624 (Zhang), hereby incorporated herein by reference in its entirety. Briefly, the LSC is computed from the first derivative of the n-second cardiac signal segment. The number of first derivative signal points having a low value, e.g. an absolute value less than a low slope threshold, is counted. The LSC is the ratio of this number of low slope signal points to the total number of first derivative signal points during the n-second segment. The low slope threshold used to compute the number of low slope signal points below the threshold can be determined from the first derivative signal. For example, the low slope threshold may be defined as a percentage, e.g., 10%, of the maximum peak of the first derivative signal.

Comparison of the LSC histograms of FIG. 4A (VF) and 4B (fast VT), show that the there is a clustering of the LSC values below approximately 0.6 during VF segments and a clustering of the LSC values above approximately 0.55 for fast VT segments. As such, a LSC threshold between approximately 0.5 and approximately 0.6 provides some degree of separation between VF and fast VT, however some overlap of the LSC values between these two rhythms exists. Separation of these two rhythms, however may not be of interest in some embodiments since both rhythms may be considered treatable (or shockable) rhythms.

The histogram in FIG. 4C of LSC values during SVT presents a clustering of LSC values above approximately 0.7. As such, a threshold between approximately 0.6 and approximately 0.7 would provide separation of VF from SVT with relatively high confidence. A threshold of approximately 0.75 would provide separation of fast VT from SVT with relatively high confidence. In both cases, however, a considerable number of values overlap between the different rhythms.

In order to further improve the confidence of a population-based threshold criterion, two or more signal characteristics may be plotted in a multi-dimensional plot to identify clusters of signal characteristic values that can be separated by a threshold defined as a continuous or discontinuous, linear or non-linear function of the plotted signal characteristic(s).

Figure 5A:
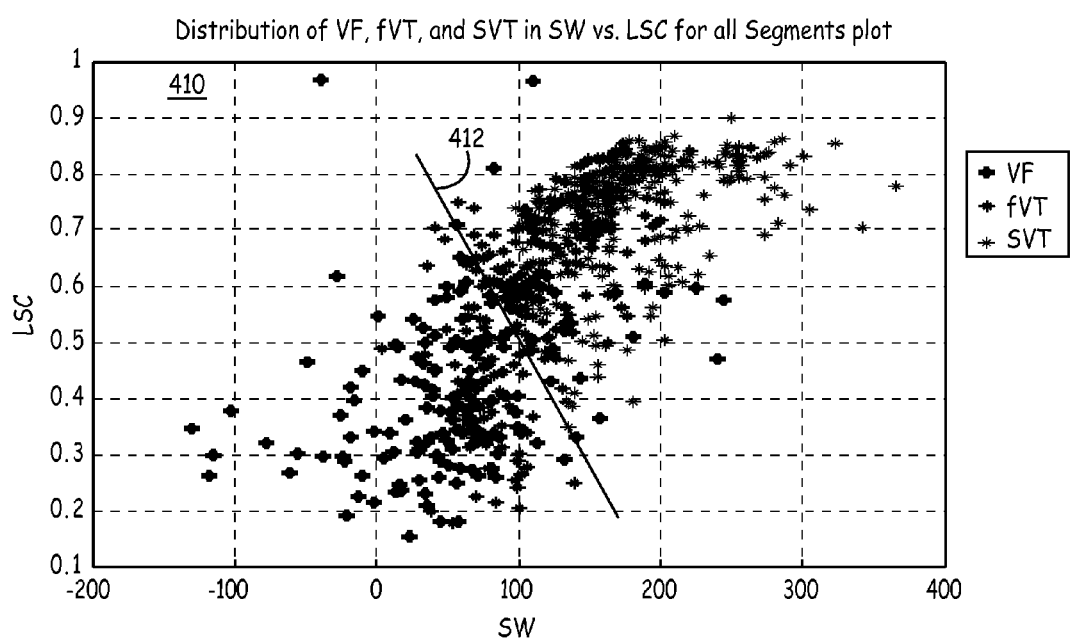
FIG. 5A is a two-dimensional plot of low slope content (LSC) plotted as a function of spectral width (SW) computed from cardiac signals obtained from a population of patients.

FIG. 5A is a two-dimensional plot 410 of LSC plotted as a function of spectral width (SW) for cardiac signal segments during different cardiac rhythms, obtained from a population of patients. SW is an approximation of the signal bandwidth. SW may be defined as the fundamental period (i.e., the inverse of the fundamental frequency or heart rate (HR)) minus the mean period (the inverse of the mean frequency). Mean frequency (MF) is calculated as the ratio of the mean absolute amplitude of the first derivative of the n-second segment to the mean absolute amplitude of the n-second segment, and the ratio is roughly proportional to the frequency of the dominant sinusoidal component in the 3-second segment.

A two-dimensional, linear threshold 412 (or a non-linear threshold) may be defined which separates the clustered points. In this example, when a threshold for LSC is defined as a linear function of SW, any LSC value falling below the threshold 412 is associated with a VF or fast VT rhythm. Virtually all points below threshold 412 correspond to treatable rhythms. As such, a corresponding cardiac signal segment may be classified as a "treatable" segment for use in cardiac event detection using threshold 412 in defining a classification criterion.

If the LSC falls above the threshold 412, there is less certainty of the rhythm type since there is considerable overlap between the values for fast VT points (treatable) and SVT points (non-treatable). The illustrative threshold 412 is therefore used to define a one-way classification criterion requiring the LSC to be less than the threshold 412. If the LSC and the SW for a cardiac signal segment results in a point less than threshold 412, the signal segment can be classified as "treatable" with a high degree of certainty since very few SVT points fall below the threshold 412.

If the LSC and the SW result in a sample point greater than the threshold 412, the threshold comparison does not meet the one-way classification criterion. Because there is considerable overlap between fast VT points and SVT points above the threshold 412, this result is inconclusive for segment classification. No segment classification would be made, and the discrimination algorithm would advance to the next threshold comparison in a sequence of one-way population-based threshold criteria.

Figure 6:
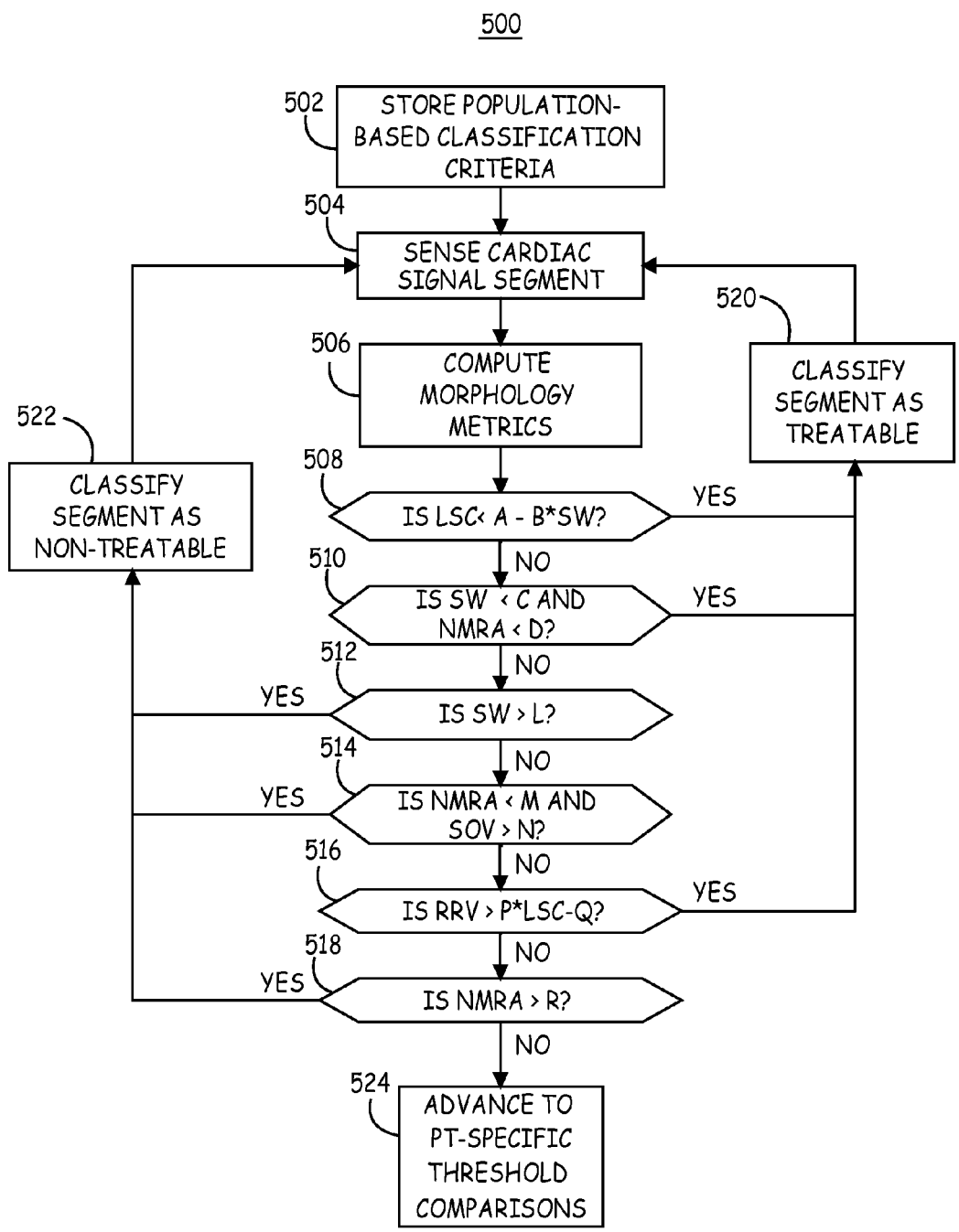
FIG. 6 is a flow chart of one embodiment of sequential comparisons made using population-based thresholds in an algorithm for detecting a cardiac event.

FIG. 6 is a flow chart 500 of one embodiment of sequential comparisons using population-based thresholds in an algorithm for detecting a cardiac event. At block 502, the population-based classification criteria are stored. The criteria are derived empirically from historical clinical data corresponding to all rhythm classifications obtained from a population of patients. The population may be as few as one patient but is typically a larger number of patients.

As will be described below, a population-based threshold criterion is stored for each classification comparison in a sequence of comparisons. Each threshold criterion is defined as a "one-way" criterion as described above.

At block 504, a cardiac signal segment is acquired and computation of morphology metrics begins at block 506. As indicated previously, all metrics or signal characteristics needed for performing all threshold comparisons in a sequence of comparisons may be computed in advance or computed only if needed as the algorithm advances through the sequence.

In the illustrative embodiment, a sequence of population-based threshold comparisons, which require relatively low processing power and time, is performed at blocks 508 through 518. If a classification criterion is satisfied, the segment is classified at block 522 or 520 without advancing through any remaining comparisons of blocks 510 through 518.

In the flow chart 500, specific examples of one-way threshold comparisons of signal characteristics are listed. These specific examples are intended to be illustrative and not limiting. In various embodiments, different signal characteristics and combinations of signal characteristics could be selected for use. Furthermore, a given classification criterion may include one or more threshold comparisons.

As used herein, a one-dimensional threshold comparison refers to the comparison between a single signal characteristic and a population-based threshold defined as a single fixed value. A one-dimensional threshold criterion is defined independent of any other signal characteristics.

A two-dimensional threshold comparison refers to the comparison between a signal characteristic and a threshold that is depending on a second signal characteristic, different than the first signal characteristic, computed for the same time segment. The threshold may be defined as a function of the second signal characteristic computed for the same time segment. A two-dimensional threshold can be defined as a linear or non-linear function of the second signal characteristic such as the two-dimensional, linear threshold 412 shown in FIG. 5A. Alternatively, a threshold may be defined for the first signal characteristic that is constrained by a threshold requirement placed on the second characteristic. This type of two-dimensional threshold comparison will be described below in conjunction with FIG. 5B.

A higher order multi-dimensional comparison could also be defined in which a first signal characteristic is compared to a threshold defined as a function of two or more different signal characteristics, which may be a polynomial or higher order function, computed during the same cardiac signal segment. Alternatively, a first signal characteristic may be compared to a fixed value threshold with constraints placed on two or more other signal characteristics as well in order for the classification criterion to be satisfied.

At block 508, a two-dimensional threshold comparison is made based on the example graph shown in FIG. 5A. The LSC computed for the current n-second signal segment is compared to a threshold defined as a linear function of SW computed for the same n-second segment. In the equation in block 508, the constant A and the coefficient B are determined empirically from the plotted patient population data for providing separation of treatable and non-treatable rhythms with high confidence.

The comparison made at block 508 is a one-way criterion for classifying treatable cardiac signal segments. If the criterion is satisfied, the segment is classified as treatable at block 520. No further comparisons at decision blocks 510 through 518 are made. If the criterion is not satisfied, i.e. if the LSC is greater than or equal to A-B*SW, the segment is not classified. A non-treatable classification is not made because a LSC greater than or equal to the threshold does not distinguish between fast VT (treatable) and SVT (non-treatable) with an acceptable level of confidence. As seen in FIG. 5A, considerable overlap exists between the cluster of fast VF points and the cluster of SVT points. The comparison performed at block 508 is therefore an example of a one-way treatable rhythm classification criterion defined as a two-dimensional, population-based threshold comparison.

At block 510, a one-way treatable rhythm classification criterion is defined as a non-linear two-dimensional threshold comparison. In this example, SW is compared to a fixed, population-based threshold C and this requirement is constrained by the requirement that the normalized mean rectified amplitude (NMRA) is less than a different fixed, population-based threshold D. In this case, the thresholds for the two different signal characteristics SW and NMRA are determined from a two-dimensional plot of SW vs. NMRA. Two fixed threshold levels may be defined for the two different signal characteristics when a particular rhythm type exhibits a clustering of points in a particular quadrant of the plot area. As such, the criterion in block 510 can be referred to as a two-dimensional criterion in that a requirement is placed on both signal characteristics based on a correlation of the two signal characteristics found by a clustering of data points in a two-dimensional plot of the two characteristics.

Figure 5B:
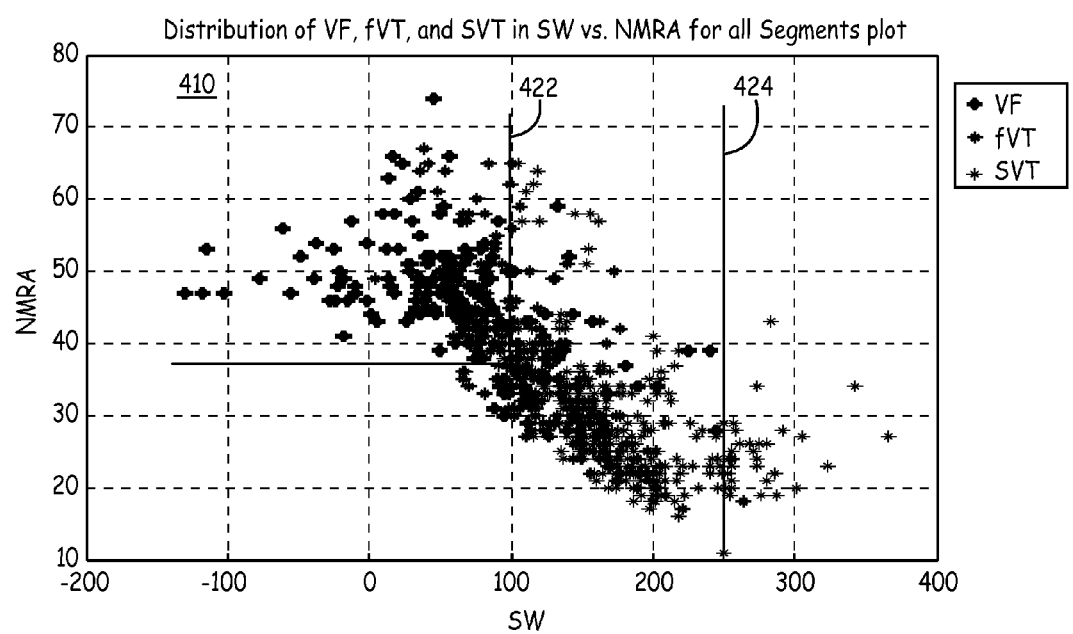
FIG. 5B is a two-dimensional plot of normalized mean rectified amplitude (NMRA) as a function of SW.

FIG. 5B is a two-dimensional plot 420 of NMRA as a function of SW. In this example, a non-linear threshold 422 separates the clustering of treatable rhythm points (including both VF and fast VT points) occurring in the upper left portion of the plot area. Below and to the right of the non-linear threshold 422, points associated with both fast VT (treatable) and SVT (non-treatable) rhythms overlap. As such, this non-linear threshold 422 based on the correlation of NMRA and SW provides a high confidence in separating a high frequency of treatable rhythms from all non-treatable rhythms but lower confidence in separating a high frequency of non-treatable rhythms from all treatable rhythms. Threshold 422 is used as a one-way threshold for classifying treatable rhythms at block

510 in FIG. 6. When satisfied, the segment is classified as treatable at block 520. When not satisfied, no classification is made and the process advances to the next criterion at block 512.

The comparison at block 512 in FIG. 6 is an example of a non-treatable rhythm classification criterion that is defined as a one-dimensional threshold comparison. Referring again to FIG. 5B, if the SW is greater than the threshold 424, virtually all plotted points are associated with SVT (non-treatable). As such, this one-dimensional threshold that is independent of other morphology metrics provides separation of non-treatable rhythms from treatable rhythms with a high degree of confidence. The constant L in block 512 is a population-based threshold, such as threshold 424 shown in FIG. 5B, derived empirically from historical clinical data to yield separation of non-treatable rhythms from treatable rhythms with a high degree of confidence.

At block 514, another example of one-way classification criterion defined as a non-linear two-dimensional threshold comparison is provided. In this case, the criterion is a non-treatable segment classification criterion. The thresholds M and N are empirically derived, population-based thresholds determined from a two-dimensional plot of NMRA vs. signal overall variability (SOV). A plot of empirically measured NMRA as a function of SOV resulted in a cluster of non-treatable rhythm points in an upper left quadrant of the plot area. The non-linear threshold thus requires NMRA to be greater than a population-based threshold and SOV less than a population-based threshold, wherein these thresholds are derived from the correlation of the plotted SOV vs NMRA. The threshold M applied to NMRA can be said to be constrained by the further requirement of SOV being greater than N in order for the classification criterion to be satisfied and result in a segment classification.

In one embodiment, SOV is calculated as the ratio of the sum of the absolute differences between signal sample point amplitudes of an n-sec segment waveform and the corresponding time-shifted n-sec segment waveform to the sum of the absolute values of the sample points in the n-sec segment. To illustrate, a 3-second segment is acquired and the RR intervals are measured and ordered from smallest to largest in a 12 RR interval buffer. The mean of the first 6 RR intervals (the smallest RR intervals in the buffer) is computed and the 3-second segment is shifted in time by half of the mean RR interval. The difference between each signal sample point in the original segment and the aligned signal sample point in the time-shifted segment is computed. The absolute values of the differences are summed SOV is then computed as the ratio of this sum of absolute differences to the sum of the absolute values of all of the sample point values in the original 3-second segment.

The threshold comparison at block 516 is another example of a two-dimensional, treatable segment classification criterion. In this example, LSC vs. RR interval variability (RRV) for a population of patients experiencing different rhythm types reveals a separation of VF from SVT points when RRV is greater than a linear threshold defined as a function LSC. The values for the coefficient P and constant Q are determined from the empirical data to provide separation of treatable rhythms from non-treatable rhythms with a high degree of confidence. Considerable overlap between fast VT and SVT points precludes separation of non-treatable from treatable fast VT rhythms making this a one-way, treatable segment classification criterion.

A final comparison in the sequence of population-based threshold criterion is applied at block 518. At block 518, a non-treatable segment classification criterion is defined by the one-dimensional, population-based threshold applied to NMRA. If the criterion is satisfied, the segment is classified as non-treatable at block 522 and is otherwise not classified.

The comparisons made at blocks 510 through 518 allow classification of a given n-second segment with a high degree of confidence and minimized computational burden by performing the comparisons that result in the highest frequency of classifications being made first. A majority of cardiac signal segments will be classified by the time the six comparisons performed at blocks 508 through 518 are completed (or earlier). Many segments will not require all six comparisons to be made since once a classification criterion is satisfied, no further comparisons in the sequence are made for that segment. After classifying the segment at either block 520 or 522, the next segment is acquired at block 504 and the comparison sequence starts again at block 508.

If none of the classification criterion are satisfied after completing the sequence of population-based threshold comparisons, the segment will remain unclassified due to the one-way nature of the threshold criteria. The process advances to more computationally intensive discrimination comparison(s) at block 524, which may involve computing a patient-specific threshold. When using a patient-specific threshold, these comparisons will require computing measurements over more than one cardiac cycle or n-second signal segment in order to obtain previous measurements from which a patient specific threshold is computed. A current measurement compared to the patient-specific threshold is computed from a most-recent cardiac signal segment and compared to a patient-specific threshold computed from an earlier-occurring cardiac signal. Specific examples of a patient-specific threshold comparison will be described in conjunction with FIG. 8.

Figure 7:
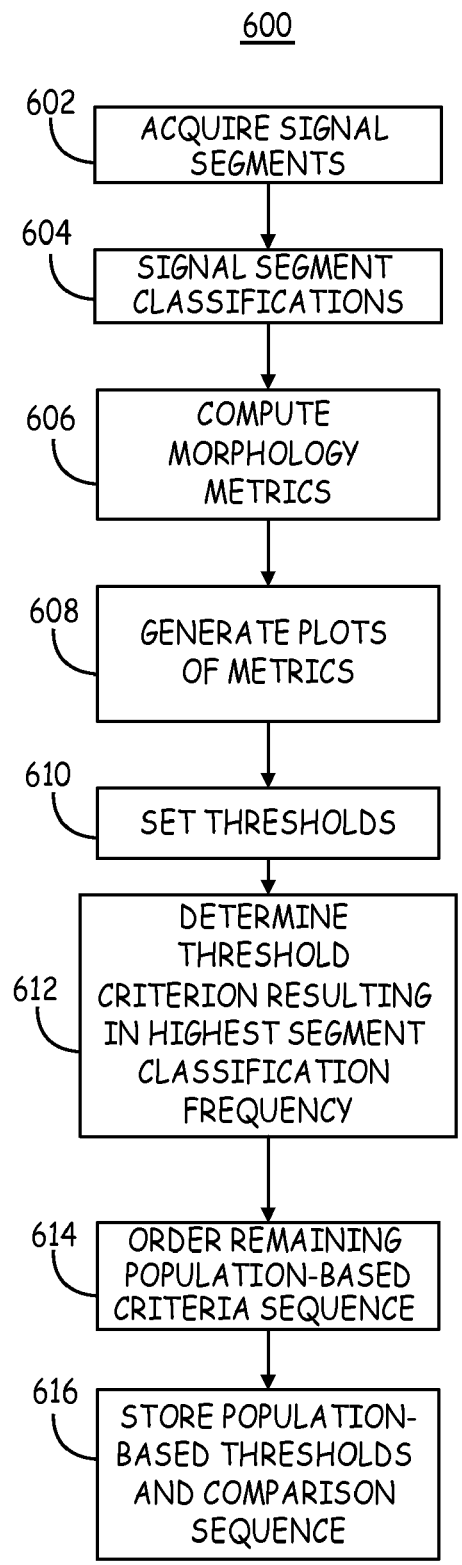
FIG. 7 is a flow chart of a method for establishing a sequence of population-based threshold comparisons for use in cardiac rhythm discrimination.

FIG. 7 is a flow chart 600 of a method for establishing a sequence of population-based threshold comparisons for use in cardiac rhythm discrimination. At block 602, historical cardiac signal segments are collected from a population of patients. The cardiac signal segments are each classified at block 604 according to a cardiac rhythm classification algorithm or manually by an expert. A classification algorithm used here may be an automated rhythm that requires high processing burden to achieve high accuracy since the process shown in FIG. 7 is performed primarily by an external computer processor. Automatically classified segments may be additionally verified by an expert. Alternatively, classification may be done exclusively by an expert.

At block 606, morphology metrics are computed for each cardiac signal segment classified at block 604. In one embodiment, LSC, SW, NMRA, SOV and RRV are computed for each segment. Other embodiments may include any of these metrics and/or other interval-based or morphological characteristics of the signal segment.

At block 608, the morphology metrics are plotted for the classified signal segments. Both one-dimensional histogram plots (e.g. as shown in FIGS. 4A-C) for each type of cardiac rhythm and/or 2D scatter plots of one metric plotted as a function of a second metric (e.g. as shown in FIGS. 5A-B) may be generated. In one embodiment, multiple two dimensional combinations of the morphology metrics listed above are plotted. In alternative embodiments, 3D plots or other even higher dimensional combinations of the morphology metrics may be generated.

At block 610, one-way classification threshold criterion are set based on the generated plots. One-dimensional thresholds may be selected visually by observing peaks and valleys between rhythm classifications in single-variable histogram plots. Two-dimensional thresholds may be selected by observing separation of clusters of treatable and non-treatable points in 2D scatter plots. Thresholds set at block 610 may alternatively be set automatically using an algorithm that identifies a threshold above or below which a high percentage (e.g. approximately 95%) of points will be classified correctly as either treatable or non-treatable.

The percentage of all segments actually resulting in a classification in response to a given threshold comparison will vary. Ideally, the percentage of segments correctly classified is high as well as the percentage of total segments classified. However, in selecting the threshold at block 610, a primary goal is to set a threshold that yields a high confidence in accuracy of the resulting classification. Obtaining a high classification yield (i.e. high percentage of all segments classified after performing a one-way threshold comparison) will be achieved through selecting metrics that present a high degree of separation between rhythm types and ordering the threshold comparisons in a sequence that most rapidly classifies the highest percentage of segments possible using the fewest population-based threshold comparisons.

The thresholds set at block 610 may include one-dimensional thresholds and two-dimensional thresholds. Thresholds may be defined to separate non-treatable segments with a high degree of certainty or to separate treatable segments with a high degree of certainty. Because considerable overlap may occur between some rhythm types, such as fast VT and SVT, any given threshold criterion is generally defined for use in treatable segment classification or non-treatable segment classification, but not both (i.e. a one-way classification criterion) as described above.

At block 612, the threshold resulting in the highest yield or highest frequency of segment classifications is identified and will be the first threshold comparison performed in a sequence of comparisons for cardiac signal classification. In one embodiment, the threshold comparison that results in the highest frequency of treatable rhythm segments being classified is identified at block 612 to be used as the first comparison in the sequence. Identification of a threshold comparison that identifies the highest frequency of treatable rhythm classifications after just one threshold comparison may allow faster and more efficient detection of a treatable cardiac event. In other embodiments, the threshold comparison resulting in the highest yield of classified segments, either treatable or non-treatable segments, may be identified at block 612.

For example, the first comparison determined at block 612 may be a classification criterion that results in at least 50% of the treatable rhythm segments being correctly classified. None of the non-treatable rhythm segments may be classified after the first threshold comparison. Priority is given to classifying the highest percentage of treatable segments as quickly as possible in order to advance efficiently toward cardiac event detection.

At block 614, the remaining thresholds are ordered based on classification yield. In this way, a sequence of population-based threshold comparisons is identified that results in classification of the highest possible percentage of segments upon each consecutive comparison in the sequence. This ordering of the threshold comparisons results in the quickest segment classification resulting in the most computationally efficient cardiac event detection. The ordering is not necessarily dependent on whether the classification is for a treatable or a non-treatable segment. In one embodiment, the goal of the comparison sequence is to classify the segment as either treatable or non-treatable using the fewest comparisons possible. The comparisons are selected to be computationally relatively simple comparisons involving one or two-dimensional thresholds applied to signal morphology metrics that, at least for the initial threshold comparisons, do not pose high computational burden on the IMD processor. In other embodiments, the comparison sequence may be prioritized to classify the highest percentage of treatable rhythm segments on each consecutive threshold comparison.

As the sequence progresses, the classification criterion may provide a lower classification yield and/or become more computationally complex. A final population-based threshold comparison may involve a relatively more complex algorithm. In one embodiment, an overall probability-correlation based method for classifying signal segments may be used as a final population-based threshold comparison in the sequence of classification criteria. The probability-correlation based method may generally correspond to methods disclosed in U.S. patent application Ser. No. 12/415,445, hereby incorporated herein by reference in its entirety. Briefly, the probability of a segment being a treatable segment is computed for each of the computed morphology metrics. The correlation coefficient between pairs of the metrics is then computed such that an overall treatable probability can be computed. The overall treatable probability is computed by summing the products of probability-based coefficients and correlation coefficient differences. This overall treatable probability is then compared to a population-based threshold.

At block 616, the population-based thresholds derived at block 610 from the patient population data and the comparison sequence determined at block 614 are stored at block 616 as a comparison sequence for use in classifying cardiac signal segments. This sequence may then be used in combination, if needed, with subsequent cardiac signal classification criteria which rely on patient-specific thresholds. The comparison sequence may be programmed into an IMD for use in a cardiac event detection algorithm.

Figure 8:
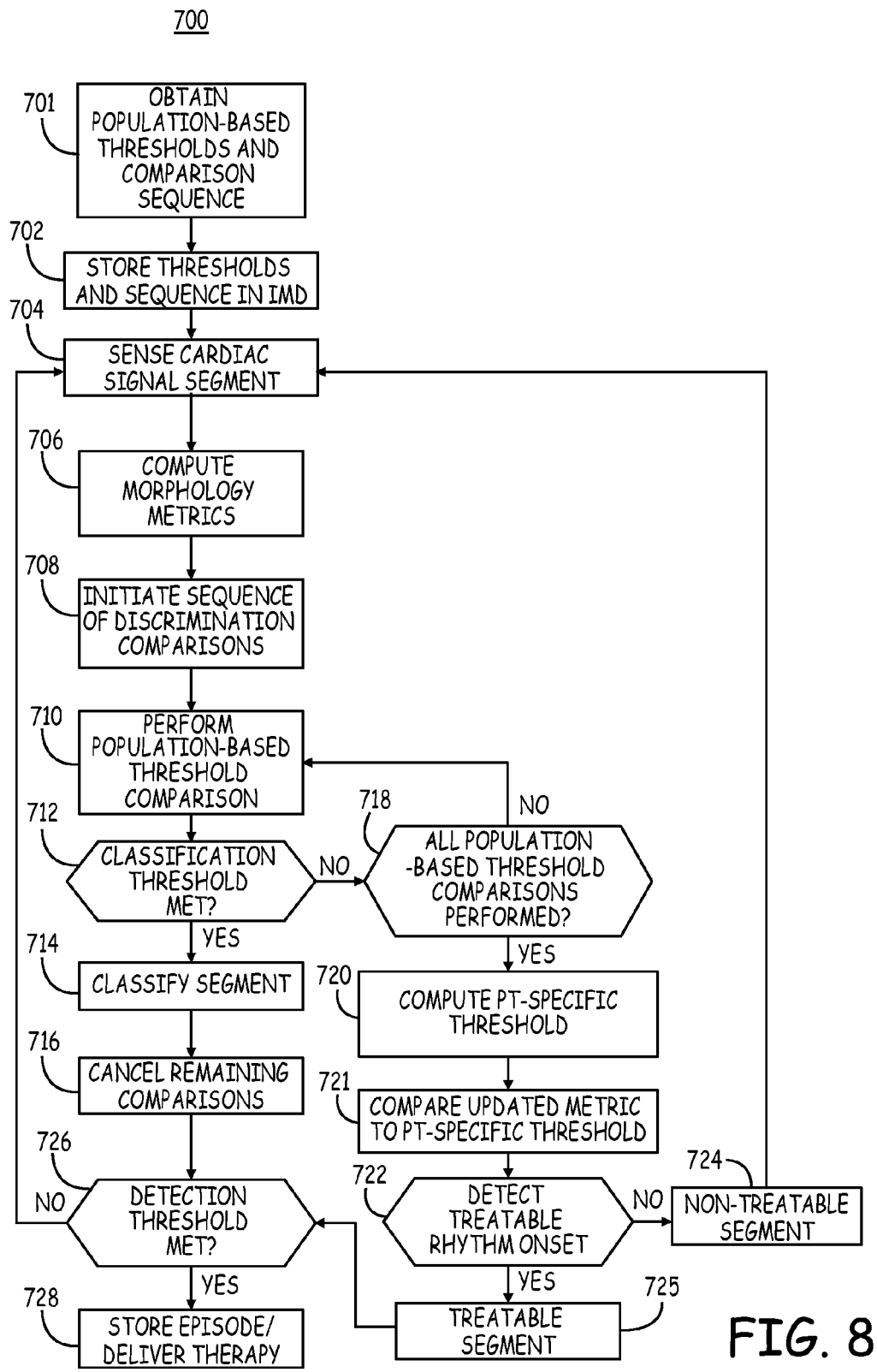
FIG. 8 is a flow chart of one method for detecting a cardiac event using a sequential discrimination of cardiac signal segments.

FIG. 8 is a flow chart 700 of one method for detecting a cardiac event using sequential discrimination of cardiac signal segments. At block 701, the population-based classification thresholds and an established sequence of population-based threshold criteria is obtained through empirical analysis of historical patient population data as described above in conjunction with FIG. 7. At block 702, the thresholds and corresponding comparison sequence is stored in an IMD being implanted in a patient for use in cardiac signal classification.

At block 704, a cardiac signal segment is sensed, and morphology metrics are computed at block 706. At block 708, the sequence of classification comparisons is initiated. Threshold comparisons at block 710 are used to determine if a one-way classification criterion in the sequence of criteria is met at block 712 as described previously. If a segment classification criterion is satisfied at block 712, the segment is classified at block 714. All remaining comparisons in the stored sequence are cancelled at block 716. A determination is made at block 726 whether cardiac event detection criteria are met. If a cardiac event is detected, the episode is stored and a therapy is delivered as appropriate at block 728.

If the entire sequence of population-based threshold criteria is applied (block 718), without yielding a segment classification, a patient-specific threshold comparison is made to classify the cardiac signal segment. A two-way patient-specific threshold comparison involves computing a characteristic of the cardiac signal during a most recent cardiac signal segment or portion thereof and computing the same characteristic for a previous portion of the same or an earlier cardiac signal segment. This allows a patient-specific change in the cardiac signal to be evaluated to determine if the change corresponds to a change from a non-treatable to a treatable rhythm.

At block 720, a rate-based or morphology based patient-specific threshold is computed. Computation of a patient-specific threshold includes computing a metric of the cardiac signal sensed in the patient and establishing the threshold using that metric. The patient-specific threshold may be computed for an earlier portion of the cardiac signal or the same portion of the cardiac signal from which the comparative measure is being taken.

If the patient-specific threshold is computed for an earlier portion of the cardiac signal, the same metric used to compute the threshold may be updated for a most recent cardiac signal segment and compared to the threshold. The patient-specific threshold determined from an earlier-occurring portion of the cardiac signal is used in a comparison to detect a change that has occurred over time in a given metric that indicates that the patient's rhythm has deteriorated to a treatable rhythm. The time period over which the change occurs may be as little as from one cardiac beat to the next or within several cardiac beats, for example up to 12 beats. The patient-specific threshold may be computed as a percentage or range of a rate or morphology metric determined for the earlier time interval, which may be within seconds or minutes of the current cardiac signal segment. At block 721, a comparison between the patient-specific threshold and the same metric computed (i.e., updated) for a most recent cardiac signal segment is made.

In one illustrative embodiment, a patient-specific evaluation of the cardiac signal is performed at block 721 to detect the onset of a treatable rhythm at block 722. The onset of a treatable rhythm is generally marked by an increase in rate, a decrease in RR interval variability, and the onset of an R-wave morphology associated with a treatable rhythm.

In this example, an increase in rate is determined using a patient-specific RR interval threshold. A rate increase may be detected by comparing a recent mean RR interval computed over a most recent time interval to a patient-specific threshold computed as a mean RR interval determined over a different, earlier time interval. If this increase in rate is one indication that a treatable rhythm onset is likely to have occurred.

A patient-specific threshold may also be defined based on a signal characteristic measured for the same time interval as the metric being compared to the patient-specific threshold. In this case, the metric being compared to the threshold is a different metric or characteristic of the signal than the metric used to compute the threshold, but would typically have the same or similar units of measure. For example, a measurement of RR interval variability for the most recent RR intervals is computed as the difference between the most recent maximum and minimum RR intervals, e.g. the maximum and minimum RR intervals out of the most recent 4 RR intervals or other number of recent intervals. If the RR interval variability is less than a percentage of the mean RR interval determined for the same most recent RR intervals, this low RR interval variability alone or combined with an increase in rate can be used to detect the onset of a treatable rhythm at block 722.

Alternatively, a patient-specific RR interval range threshold may be computed as a difference between a maximum and minimum interval for a previous time interval and compared to the RR interval range computed for a most recent time interval. If an increase in rate is detected based on a patient-specific rate threshold (as opposed to a nominally defined or population based threshold) and a decrease in RR interval variability based on a patient-specific variability threshold is detected, a treatable rhythm onset may be detected at block 722.

Additionally or alternatively, rate onset detection at block 720 may require the detection of a change in R-wave morphology. An R-wave morphology metric may be computed for a most recent R-wave or group of R-waves and compared to the same metric computed for a previous R-wave or group of R-waves. If the R-wave morphology metric for the most recent R-wave(s) exhibits a change compared to the patient-specific threshold computed from an earlier time interval, the beat morphology change supports the detection of a treatable rhythm onset at block 720. The detection of a treatable rhythm onset using a rate onset metric and a beat morphology onset metric may use methods generally disclosed in U.S. patent application Ser. No. 12/430,301, hereby incorporated herein by reference in its entirety.

A patient-specific morphology based threshold may be related to a specific beat feature, such as a slope, amplitude, slew rate, width, or the like. Other morphology-based patient-specific thresholds may be determined using an overall beat morphology, such as a wavelet analysis as generally described in U.S. Pat. No. 6,393,316 (Gillberg), hereby incorporated herein by reference in its entirety.

The two-way threshold comparison performed at block 721 will result in a classification of the cardiac signal segment. If the treatable rhythm onset detection criteria are not satisfied at block 722, based on the comparison at block 721, the segment is classified as non-treatable. If the treatable rhythm onset detection criteria are satisfied at block 722, the segment is classified as treatable at block 725. As such, after completion of the patient-specific threshold comparison, all cardiac signal segments will be classified.

Classification criteria applied at block 722 which includes at least one patient-specific threshold criterion, will always result in a segment classification at one of blocks 724 or 725. In contrast, a classification criterion applied at block 712 that is defined using a population-based threshold may or may not result in a segment classification. Additional comparisons must be performed. The patient-specific threshold is used in a two-way classification criterion that results in a classification of all remaining segments that have not been classified after performing the one-way population-based threshold comparisons.

If a non-treatable classification is made at block 724, a cardiac event will not be detected for the current cardiac signal segment. The process returns to block 704 to begin the process of classifying the next cardiac signal segment.

If the segment is classified as treatable at block 725, the segment may cause a cardiac detection threshold to be met at block 726. If so, the detected event is stored at block 728 and a therapy may be delivered if appropriate. If the cardiac event detection threshold is not met at block 726, the process returns to block 704.

Thus, a medical device and associated method for detecting cardiac events have been presented in the foregoing description with reference to specific embodiments. It is appreciated that various modifications to the referenced embodiments may be made without departing from the scope of the disclosure as set forth in the following claims.

The invention claimed is:

1. A method of classifying cardiac signals according to a cardiac event type, comprising:
    establishing a plurality of population-based thresholds corresponding to a plurality of cardiac signal morphology metrics for discriminating between a first cardiac event and a second cardiac event;
    establishing a first threshold criterion for discriminating cardiac events, the first threshold criterion comprising a comparison between a cardiac signal morphology metric and one established population-based threshold of the established plurality of population-based thresholds;

sensing a cardiac signal segment in a patient;
applying the first threshold criterion to the sensed cardiac signal segment;
classifying the cardiac signal segment only in response to the applying the first threshold criterion being satisfied;
establishing a patient-specific threshold in response to the sensed cardiac signal segment not being classified after applying the first threshold criterion;
computing a metric of the sensed cardiac signal segment and comparing the metric to the established patient-specific threshold; and
classifying the sensed signal segment in response to the comparing of the metric to the established patient-specific threshold.

2. The method of claim 1, further comprising:
establishing a sequence of population-based threshold criteria;
advancing to a next population based threshold criterion in the sequence in response to the first threshold criterion not being satisfied;
classifying the sensed cardiac signal segment in response to the earliest criterion in the sequence being satisfied; and
cancelling a remaining population-based threshold criterion in the sequence in response to classifying the cardiac signal segment.

3. The method of claim 2, wherein establishing a sequence of population-based threshold criteria comprises determining the first threshold criterion as one of the population-based threshold criteria that results in a highest frequency of cardiac signal segment classifications.

4. The method of claim 3, wherein the highest frequency of cardiac signal segment classifications comprises a highest frequency of a treatable cardiac signal segment classification.

5. The method of claim 1, wherein establishing the plurality of population-based thresholds comprises:
sensing a cardiac signal for a plurality of time segments in a population of patients;
determining the plurality of morphology metrics for each of the plurality of time segments;
classifying each of the plurality of time segments according to a cardiac event;
plotting the plurality of morphology metrics for the classified time segments; and
defining a population-based threshold that substantially separates a first cluster of classified cardiac signal time segments from a second cluster of classified cardiac signal time segments.

6. The method of claim 5, wherein establishing a plurality of population-based thresholds comprises:
plotting a multi-dimensional scatter plot of at least two of the plurality of morphology metrics for the plurality of classified cardiac signal time segments; and
defining a population-based threshold for one of the plurality of morphology metrics as a function of another of the plurality of morphology metrics based on the multi-dimensional plot, the threshold defined to separate the first cluster of classified cardiac signal time segments from the second cluster of classified cardiac signal time segments.

7. The method of claim 6, wherein the second cluster of classified cardiac signal segments overlaps a third cluster of classified cardiac signal segments, the established population-based threshold defining a one-way classification criterion for classifying only the first cluster of cardiac signal segments in response to the population-based threshold.

8. The method of claim 1, wherein the plurality of cardiac signal morphology metrics comprises at least one of a low slope content, a normalized mean rectified amplitude, a spectral width, a signal overall variability, and an RR interval variability.

9. The method of claim 1, wherein establishing a patient-specific threshold comprises computing a characteristic of an earlier-occurring cardiac signal segment.

10. The method of claim 1, wherein establishing a patient-specific threshold comprises computing a characteristic of a currently occurring cardiac signal segment.

11. The method of claim 1, wherein establishing a patient-specific threshold comprises:
establishing a classification threshold for detecting a treatable rhythm onset;
classifying the sensed cardiac signal segment as treatable in response to the established classification threshold for detecting a treatable rhythm onset being detected; and
classifying the sensed cardiac signal segment as non-treatable in response to the established classification threshold for detecting a treatable rhythm onset not being detected.

12. The method of claim 1, wherein establishing a plurality of population-based thresholds comprises determining a correlation between a first one of the plurality of morphology metrics determined for a time segment and a second one of the plurality of morphology metrics determined for the same time segment.

13. A medical device system for classifying cardiac signals according to a cardiac event type, comprising:
a processor configured to
establish a plurality of population-based thresholds corresponding to a plurality of cardiac signal morphology metrics for discriminating between a first cardiac event and a second cardiac event, and
establish a first threshold criterion for discriminating cardiac events, the first threshold criterion comprising a comparison between a cardiac signal morphology metric and one established population-based threshold of the plurality of population-based thresholds;
a plurality of electrodes for sensing a cardiac signal segment;
a programmable memory storing the first population-based threshold criterion; and
a controller configured to:
apply the first threshold criterion to the sensed cardiac signal segment;
classify the sensed cardiac signal segment only in response to the applying the first threshold criterion being satisfied;
establish a patient-specific threshold in response to the sensed cardiac signal segment not being classified after applying the first threshold criterion;
compute a metric of the sensed cardiac signal segment and comparing the metric to the established patient-specific threshold; and
classify the sensed cardiac signal segment in response to the comparing of the metric to the established patient-specific threshold.

14. The system of claim 13, wherein the processor is further configured to establish a sequence of population-based threshold criteria; and
the controller is configured to advance to a next population based threshold criterion in the sequence in response to the first threshold criterion not being satisfied, classify the sensed cardiac signal segment in response to the earliest criterion in the sequence being satisfied, and cancel a remaining population-based threshold criterion in the sequence in response to classifying the cardiac signal segment.

15. The system of claim 14, wherein establishing a sequence of population-based threshold criteria comprises determining a first one of the population-based threshold criteria that results in a highest frequency of cardiac signal segment classifications.

16. The system of claim 15, wherein the highest frequency of cardiac signal segment classifications comprises a highest frequency of a treatable cardiac signal segment classification.

17. The system of claim 13, wherein establishing the plurality of population-based thresholds comprises:
sensing a cardiac signal for a plurality of time segments in a population of patients;
determining the plurality of morphology metrics for each of the plurality of time segments;
classifying each of the plurality of time segments according to a cardiac event;
plotting the plurality of morphology metrics for the classified time segments; and
defining a population-based threshold that substantially separates a first cluster of classified cardiac signal time segments from a second cluster of classified cardiac signal time segments.

18. The system of claim 17, wherein establishing a plurality of population-based thresholds comprises
plotting a multi-dimensional scatter plot of at least two of the plurality of morphology metrics for the plurality of classified cardiac signal time segments; and
defining a population-based threshold for one of plurality of morphology metrics as a function of another of the plurality of morphology metrics based on the multi-dimensional plot, the threshold defined to separate the first cluster of classified cardiac signal time segments from the second cluster of classified cardiac signal time segments.

19. The system of claim 18, wherein the second cluster of classified cardiac signal segments overlaps a third cluster of classified cardiac signal segments, the established population-based threshold defining a one-way classification criterion for classifying only the first cluster of cardiac signal segments in response to the population-based threshold.

20. The system of claim 13, wherein the plurality of cardiac signal morphology metrics comprises at least one of a low slope content, a normalized mean rectified amplitude, a spectral width, a signal overall variability, and an RR interval variability.

21. The system of claim 13, wherein establishing a patient-specific threshold comprises computing a characteristic of an earlier-occurring cardiac signal segment.

22. The system of claim 13, wherein establishing a patient-specific threshold comprises establishing a classification threshold for detecting a treatable rhythm onset, and wherein the controller is further configured to classify the sensed cardiac signal segment as treatable in response to the established classification threshold for detecting a treatable rhythm onset being detected, and classify the sensed cardiac signal segment as non-treatable in response to the established classification threshold for detecting a treatable rhythm onset not being detected.

23. The system of claim 13, wherein establishing a plurality of population-based thresholds comprises determining a correlation between a first one of the plurality of morphology metrics determined for a time segment and a second one of the plurality of morphology metrics determined for the same time segment.

24. The system of claim 13, wherein establishing a patient-specific threshold comprises computing a characteristic of a currently occurring cardiac signal segment.

25. A non-transitory computer-readable medium storing a set of instructions which cause a processor of a medical device system to:
establish a plurality of population-based thresholds corresponding to a plurality of cardiac signal morphology metrics for discriminating between a first cardiac event and a second cardiac event;
establish a first threshold criterion for discriminating cardiac events, the first threshold criterion comprising a comparison between a cardiac signal morphology metric and one established population-based threshold of the established plurality of population-based thresholds;
sense a cardiac signal segment;
apply the first threshold criterion to the sensed cardiac signal segment;
classify the sensed cardiac signal segment only in response to the applying the first threshold criterion being satisfied;
establish a patient-specific threshold in response to the sensed cardiac signal segment not being classified after applying the first threshold criterion;
compute a metric of the sensed cardiac signal segment and comparing the metric to the established patient-specific threshold; and
classify the sensed signal segment in response to the comparing of the metric to the established patient-specific threshold.

* * * * *